United States Patent
Bunke et al.

(10) Patent No.: US 7,591,263 B2
(45) Date of Patent: Sep. 22, 2009

(54) DEVICE FOR DIFFERENTIAL PRESSURE MEASUREMENT IN ANESTHETIC DISPENSING DEVICES

(75) Inventors: Claus Bunke, Sereetz (DE); Matthias Witt, Bad Schwartau (DE); Rainer Kunz, Lübeck (DE); Jürgen Müller, Lübeck (DE); Sven Heyer, Lübeck (DE); Heye Harms, Stockelsdorf (DE); Uwe Schmidt, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 835 days.

(21) Appl. No.: 11/169,195

(22) Filed: Jun. 28, 2005

(65) Prior Publication Data

US 2006/0060000 A1  Mar. 23, 2006

(30) Foreign Application Priority Data

Sep. 21, 2004  (DE) ................. 10 2004 045 733

(51) Int. Cl.
*A61M 16/00* (2006.01)
(52) U.S. Cl. .................. 128/203.12; 128/204.21
(58) Field of Classification Search ......... 128/203.12, 128/204.21, 204.22, 204.18, 203.25; 73/861.52
See application file for complete search history.

(56) References Cited

U.S. PATENT DOCUMENTS

| | | | | |
|---|---|---|---|---|
| 4,633,705 A | * | 1/1987 | Merilainen et al. | 73/31.04 |
| 4,651,730 A | * | 3/1987 | von dem Hagen et al. | 128/204.21 |
| 5,237,990 A | * | 8/1993 | Psaros et al. | 128/204.21 |
| 5,411,019 A | | 5/1995 | Smith | |
| 5,592,934 A | | 1/1997 | Thwaites | |

FOREIGN PATENT DOCUMENTS

EP  0 657 183 A1  6/1995

\* cited by examiner

*Primary Examiner*—Steven O Douglas
(74) *Attorney, Agent, or Firm*—McGlew and Tuttle, P.C.

(57) ABSTRACT

A device is provided for measuring the differential pressure in anesthetic dispensing devices, with which the differential pressure can be measured between two lines (2, 6) for supplying gaseous components to a mixing site (3). The device has at least one differential pressure sensor (11), which is connected with the lines (2, 6) for supplying the gaseous components. Buffer elements (12, 12') are integrated in the connection between the lines (2, 6) for supplying the gaseous components and the differential pressure sensor (11).

20 Claims, 2 Drawing Sheets

DEVICE FOR DIFFERENTIAL PRESSURE MEASUREMENT IN ANESTHETIC DISPENSING DEVICES

CROSS REFERENCE TO RELATED APPLICATIONS

This application claims the benefit of priority under 35 U.S.C. § 119 of German Application DE 10 2004 045 733.6 filed Sep. 21, 2004, the entire contents of which are incorporated herein by reference.

FIELD OF THE INVENTION

The present invention pertains to a device for measuring the differential pressure in anesthetic dispensing devices with a differential pressure sensor protected from overload caused by rapid changes in pressure. Such devices can be used wherever the measurement of a differential pressure becomes necessary during the dispensing of anesthetics.

BACKGROUND OF THE INVENTION

A frequently applied principle of anesthetic dispensing is based on the separate supply of anesthetic gases and fresh gas to a mixing site. The gaseous components are sent here through a pipe system, in which various flow resistances are integrated. The fresh gas is fed to the mixing site via a line in which a fixed flow resistance, a so-called bypass, is integrated. The anesthetic gas is fed via a line, in which a variable flow resistance, which is used to dispense the anesthetic gas, is integrated. The two lines meet at the mixing site. The mixing of the gaseous components takes place there. The gas mixture is fed to the patient away from the mixing site.

The anesthetic gas is dispensed by varying the variable flow resistance of the dispensing device. A constant mixing ratio of the anesthetic gas to the fresh gas is desirable here. Such a system is therefore usually calibrated such that in case of correct dispensing of the anesthetic, the same pressure prevails in front of the two flow resistances, namely, the bypass and the variable flow resistance of the dispensing device.

The maintenance of this state is monitored by a differential pressure sensor, which detects the pressure in both lines. The measured differential pressure equals zero in the ideal case. However, very low pressure values are maintained in the normal case of operation.

The sensitivity of the differential pressure sensor used for this differential pressure measurement is therefore usually very high, which leads to a narrow measuring range at very good accuracy of measurement. Highly accurate monitoring of the mixing ratios can thus be guaranteed. One drawback of such a device is that suddenly occurring higher differential pressures may lastingly damage a differential pressure sensor designed for such a sensitivity when its measuring range is exceeded.

A stable state of flow becomes established in the system of supply lines supplying the gaseous components to the mixing site in case of normal operation. A negligibly low differential pressure becomes established at the differential pressure sensor in this stable state of flow.

If there is an undesired disturbance of this stable state of flow for various reasons, the individual branches of the supply lines are not able, because of the different flow resistances integrated in them, to respond to these changes or disturbances with the same time constant. A new state of flow will consequently become established with different delays in the individual branches of the line. Differential pressures, which exceed the measuring range of the differential pressure sensor by several times, may develop at the differential pressure sensor during this setting time. A long-lasting difference in the pressures present is, by contrast, not possible, because the supply lines are connected with one another at the mixing site and thus form a pneumatic short-circuit.

However, the brief occurrence of high differential pressures is sufficient to inflict lasting damage to the sensitive differential pressure sensor. It is possible, for example, that the connection in the direction of the patient will be briefly closed. This leads to a rapid rise in the pressure in the system, which can maximally correspond to the pressure of the fresh gas supply system. If the system is opened again, an equally rapid release will occur. These dynamic processes do not lead to equal changes in pressure at the same time at the two points at which pressure is tapped, at which the differential pressure sensor is connected with the lines for supplying the gaseous component, because of the differences in the flow resistances of the bypass and the variable flow resistance. Consequently, great differential pressures will build up for a short time.

SUMMARY OF THE INVENTION

The object of the present invention is therefore to effectively prevent damage to the differential pressure sensor due to brief peaks in the differential pressure.

The present invention comprises a device for measuring the differential pressure in anesthetic dispensing devices, with which the differential pressure between two lines for supplying gaseous components to a mixing site can be measured, and which contains at least one differential pressure sensor, which is connected with the lines for supplying the gaseous components, wherein buffer elements are integrated in the connection between the lines for supplying the gaseous components and the differential pressure sensor. The volumes of these buffer elements are advantageously selected, in conjunction with the flow resistance of means that limit the inflow of the gaseous components into the buffer volumes, to be such that a response characteristic that is characterized by time constants that are higher than the time constants that characterize the response characteristic of the lines for supplying the gaseous components will develop in the interior of the buffer elements during changes in pressure. It is especially advantageous if the characteristic response times in the interior of the buffer elements are higher than the characteristic response times in the lines for supplying the gaseous components by at least one order of magnitude.

The differential pressure sensor is connected, as a rule, with a line for supplying fresh gas and with a line for supplying a gaseous anesthetic. The connection between the lines for supplying the gaseous components and the differential pressure sensor is advantageously embodied in terms of design such that the flow paths between the lines for supplying the gaseous components and the buffer elements have a higher flow resistance than the line for supplying the anesthetic gas. This can be embodied, for example, when the buffer elements have themselves means that determine the flow resistance of the flow paths between the lines for supplying the gaseous components and the buffer elements. Such means for determining the flow resistance may also be arranged upstream of the buffer elements.

In an advantageous embodiment, the means that determine the flow resistance of the flow paths between the lines for supplying the gaseous components and the buffer elements comprise apertures, through which the gaseous components can flow into the buffer elements.

The great advantage of the device according to the present invention is that briefly occurring peaks in the differential pressure do not exert any damaging effect on the differential pressure sensor and the function of this sensor is thus preserved. The buffer elements and the flow resistances limiting the filling of the buffer elements are dimensioned such that the time that would be necessary to reach the maximum pressure in the interior of the particular buffer element is longer than the time during which the pressure differences occur in the entire pipe system at all. It was found in the case of typical gas flows that occur in anesthetic dispensing devices that an effective device is obtained already when apertures used to set the flow resistance at the inlet of the buffer elements have a diameter of at most 150 μm and the buffer elements themselves have a volume of at least 0.2 mL.

In an especially advantageous embodiment of a device according to the present invention, the buffer elements have a volume of 1 mL. On the side facing away from the differential pressure sensor, the buffer elements have apertures that have a diameter of 100 μm each. The buffer elements are in connection via these apertures with the lines for supplying the gaseous components. Together with the apertures or other means for increasing the flow resistance, the buffer elements form damping elements.

The device according to the present invention consequently comprises at least two damping elements, which are arranged between the tapping points in the lines for supplying the gaseous components and the signal inputs of the differential pressure sensor. These damping elements comprise essentially a volume that can be filled via a flow resistance, i.e., for example, a small aperture. The aperture limits the volume on the side of the tapping point. The differential pressure sensor is connected, by contrast, with the damping elements via measuring lines without additional flow resistances. The mass flow through the apertures is markedly smaller than that through the bypass and that through the variable flow resistance, always at equal pressure difference. The damping elements may be embodied by a special shape of the connection lines, which connect the differential pressure sensor with the lines for supplying the gaseous components. A narrow part of the connection lines is dimensioned for this purpose such that it acts essentially as a limiting flow resistance, whereas another part with a larger cross section acts as a buffer element.

In case of a sudden closure or opening of the mixed gas line, nearly the same behavior will develop in the system up to the location of the apertures as without the damping elements. However, this behavior is not passed on directly to the differential pressure sensor. The small mass flow through the apertures delays the build-up of pressure in the volumes of the buffer elements in front of the differential pressure sensor and leads to a slower and more uniform pressure build-up or pressure drop at the measuring inputs of the differential pressure sensor. Before the maximum pressure difference can build up in front of the signal inputs, a pressure equilibrium will already have become established in the entire system, which leads to the prevention of a further rise of the differential pressure. This leads, as a whole, to lower maximum values of the pressure difference present at the differential pressure sensor, which are detected by this sensor. A reduction of the aperture opening or an increase in the volumes in front of the differential pressure sensor or both leads to an intensification of the damping effect. It was found that very good damping action is obtained in case of aperture diameters of 100 μm and a buffer element volume of 1 mL. However, the delay of the signal build-up at the differential pressure sensor, which is associated with this, continues to permit reliable dispensing of anesthetics to be guaranteed during the normal operation.

The present invention will be explained in greater detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
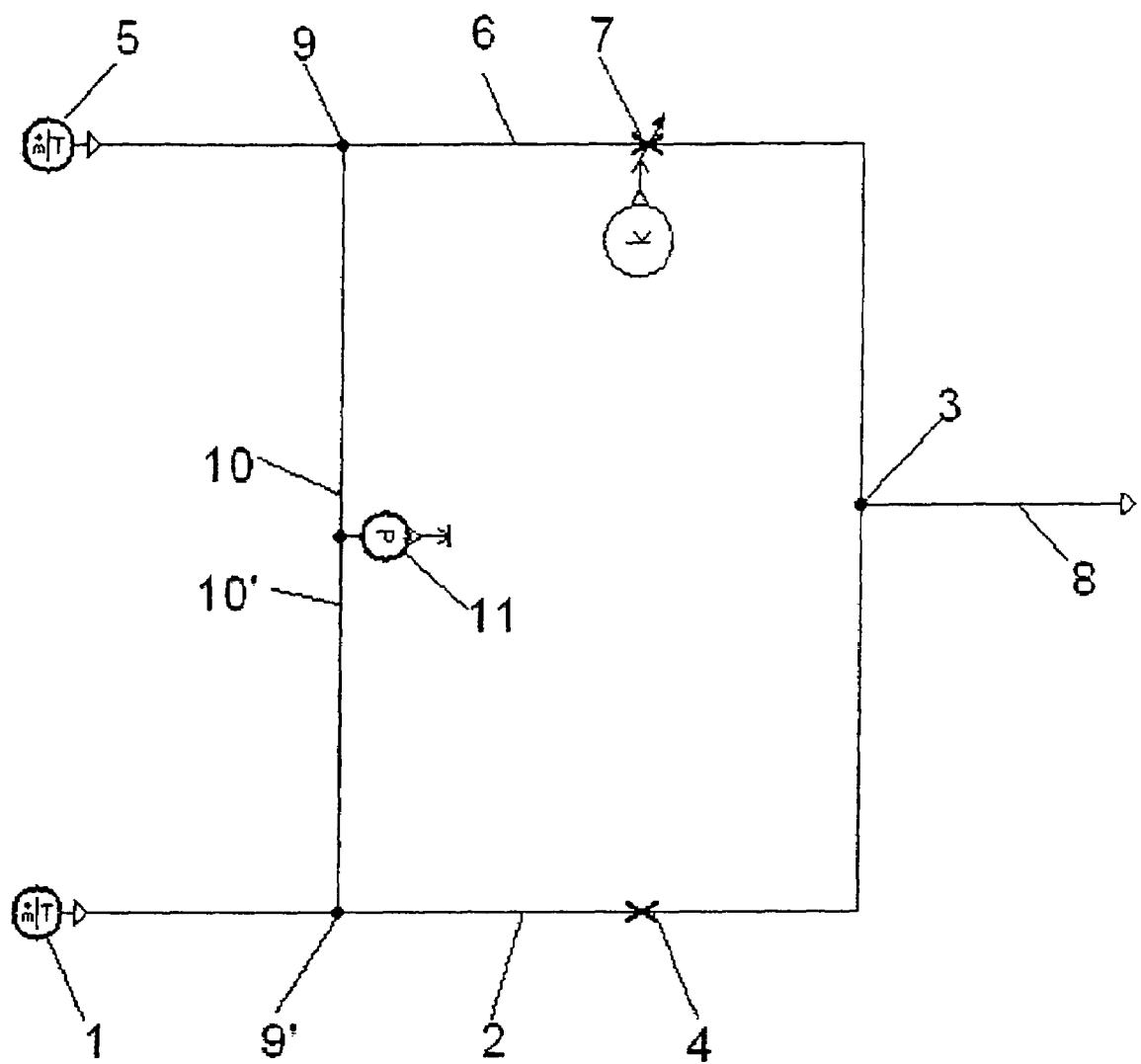
FIG. 1 is a diagram showing a device for measuring the differential pressure in anesthetic dispensing devices according to the state of the art.

Referring to the drawings in particular, FIG. 1 shows a schematic view of a device for measuring the differential pressure in anesthetic dispensing devices. A fresh gas line 2 leads from a fresh gas supply unit 1 to a mixing site 3. A fixed resistance, a so-called bypass 4, is integrated within the fresh gas line 2. A gaseous anesthetic supply unit 5 is connected with the mixing site 3 via a gaseous anesthetic line 6. A variable flow resistance 7 is integrated within the anesthetic gas line 6. The gaseous components are mixed at the mixing site 3. The gas mixture formed there is passed on in the direction of the patient in a mixed gas line 8. Branches 9, 9', at which the pressure to be measured can be tapped, are located between the gas supply units 1, 5 and the flow resistances 4, 7. Measuring lines 10, 10', which connect the tapping points with a differential pressure sensor 11, are arranged at these branches 9, 9' acting as tapping points. The system is calibrated such that the same pressure becomes established in front of the fixed flow resistance 4 and the variable flow resistance 7 during normal operation. This can sometimes be achieved with markedly different flow resistances only. If a closure develops in the line 8, a pressure that corresponds to the pressure of the gas supply unit with the higher pressure will become established in the entire line system. However, this pressure rise will not take place simultaneously in all parts of the line. There will rather be pressure increases at different rates due to the different flow resistances 4 and 7, which causes that markedly different pressures can prevail between the point in time at which the closure develops in line 8 and the time at which the maximum end pressure is reached in the fresh gas line 2 and in the gaseous anesthetic line 6. The pressure difference is present to its full extent at the differential pressure sensor 11. If this pressure difference exceeds the measuring range of the differential pressure sensor 11, this may be damaged or destroyed. Similarly great differences in pressure may also develop in case of a sudden relief of the line system, i.e., for example, during the sudden opening of line 8 after a preceding pressure rise.

Figure 2:
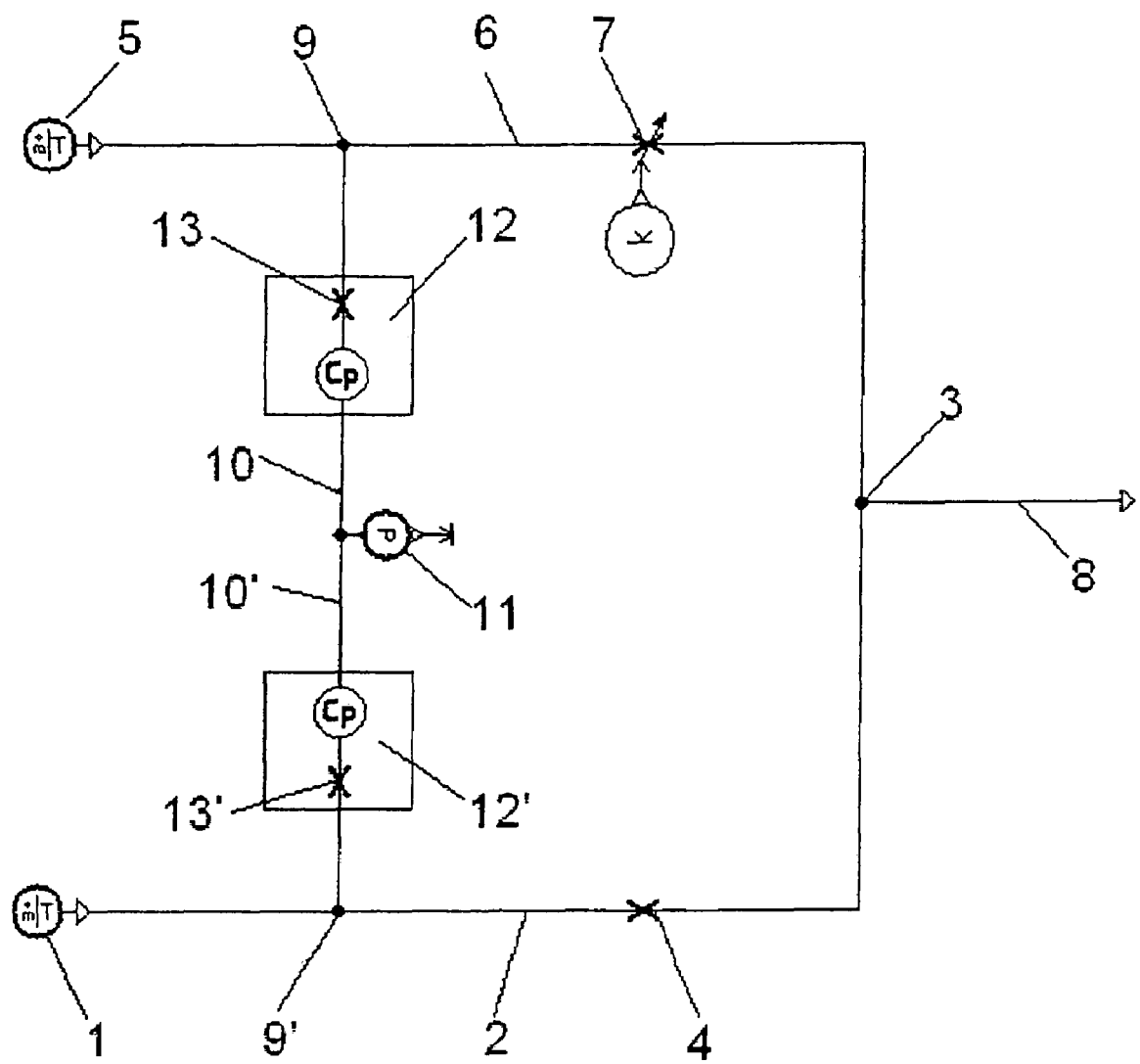
FIG. 2 is a diagram showing a device according to the present invention for measuring the differential pressure in anesthetic dispensing devices.

FIG. 2 shows a device according to the present invention for measuring the differential pressure in anesthetic dispensing devices. As with the device of FIG. 1, A fresh gas line 2 leads from a fresh gas supply unit 1 to a mixing site 3. A fixed resistance, a so-called bypass 4, is integrated within the fresh gas line 2. A gaseous anesthetic supply unit 5 is connected with the mixing site 3 via a gaseous anesthetic line 6. A variable flow resistance 7 is integrated within the anesthetic gas line 6. The gaseous components are mixed at the mixing site 3. The gas mixture formed there is passed on in the direction of the patient in a mixed gas line 8. Branches 9, 9' are provided at which the pressure to be measured can be tapped. The branches 9, 9', are located between the gas supply units 1, 5 and the flow resistances 4, 7. A differential pressure sensor 11 is provided in the measuring lines 10, 10' that connect with branches 9, 9' acting as tapping points. The measuring lines 10, 10' have buffer elements 12, 12' integrated therein, according to the present invention. The flow paths between the lines for supplying the gaseous components and the buffer elements have a higher flow resistance than the line for supplying the gaseous anesthetic. This increase in the flow resistance is achieved by the buffer elements 12, 12' having additional components for increasing the flow resistance, which essentially determine the flow resistance of the flow paths between the lines for supplying the gaseous components and the buffer elements. This increase in the flow resistance may be embodied, for example, by the use of apertures 13, 13', through which the gaseous components can flow into the buffer elements 12, 12'.

The effectiveness of the buffer elements depends essentially on their dimensioning. The device thus equipped damps the increase and decrease in the pressure, which takes place at different rates, in front of the signal inputs of the differential pressure sensor 11 in case of a sudden closure or a sudden opening of the drain line in the direction of the patient. As a result, the time behavior becomes more similar at the two signal inputs and the resulting pressure difference will become smaller. If the device is dimensioned correctly, the maximum pressure differences will not exceed the preset limits at the differential pressure sensor 11. Furthermore, it is possible to keep the pressure differences occurring within the measuring range of the differential pressure sensor 11, which makes possible the continuous monitoring of the differential pressure even during disturbances.

While a specific embodiment of the invention has been shown and described in detail to illustrate the application of the principles of the invention, it will be understood that the invention may be embodied otherwise without departing from such principles.

What is claimed is:

1. A device for measuring the differential pressure in anesthetic dispensing devices, the device comprising:
    two lines for supplying gaseous components to a mixing site;
    a differential pressure sensor;
    connections of said differential pressure sensor with said two lines for supplying the gaseous components, said differential pressure sensor for measuring a differential pressure between said two lines for supplying gaseous components to said mixing site; and
    buffer elements, each of said buffer elements being integrated in a respective one of said connections between a respective one of said two lines for supplying the gaseous components and said differential pressure sensor.

2. A device in accordance with claim 1, further comprising a flow resistance associated with each of said buffer elements for limiting an influx of the gaseous components into volumes of respective said buffer elements wherein the volumes of said buffer elements are dimensioned, in conjunction with the flow resistance, such that a response behavior, to changes in pressure, that is characterized by time constants that are higher than the time constants that characterize the response behavior, to changes in pressure, of said lines for supplying the gaseous components will develop in the interior of said buffer elements during changes in pressure.

3. A device in accordance with claim 1, wherein characteristic response times to pressure changes in the interior of said buffer elements are longer than the characteristic response times to pressure changes in said lines for supplying the gaseous components, by at least one order of magnitude.

4. A device in accordance with claim 1, wherein said two lines comprise a line for supplying fresh gas and a line for supplying a gaseous anesthetic.

5. A device in accordance with claim 4, wherein flow paths, between said lines for supplying the gaseous components and said buffer elements, have a higher flow resistance than a flow resistance of said line for supplying the gaseous anesthetic.

6. A device in accordance with claim 1, wherein said buffer elements include flow resistance means that determine a flow resistance of flow paths of said connections between said lines for supplying the gaseous components and said buffer elements.

7. A device in accordance with claim 6, wherein said flow resistance means comprise apertures through which the gaseous components can flow into said buffer elements.

8. A device in accordance with claim 7, wherein said apertures have a diameter of at most 150 μm and said buffer elements have a volume of at least 0.2 mL.

9. A device in accordance with claim 7, wherein said apertures have a diameter of 100 μm and said buffer elements have a volume of 1 mL.

10. An anesthetic dispensing device arrangement, comprising:
    a fresh gas supply unit;
    a fresh gas line with a fixed resistance, said fresh gas line being connected to said fresh gas supply unit;
    a gaseous anesthetic supply unit;
    a gaseous anesthetic line with a variable flow resistance, said gaseous anesthetic line being connected to said gaseous anesthetic supply unit and each of said gaseous anesthetic line and said fresh gas line is connected at a mixing site;
    a differential pressure sensor;
    a fresh gas line connection from said fresh gas line to said differential pressure sensor;
    a gaseous anesthetic line connection from said gaseous anesthetic line to said differential pressure sensor, said differential pressure sensor measuring a differential pressure between said fresh gas line and said gaseous anesthetic line;
    a fresh gas line connection buffer element integrated in said fresh gas line connection; and
    a gaseous anesthetic line connection buffer element integrated in said gaseous anesthetic line connection.

11. An anesthetic dispensing device arrangement in accordance with claim 10, further comprising a first buffer flow resistance associated with said fresh gas line connection buffer element for limiting an influx of the gaseous components into a fresh gas volume of said fresh gas line connection buffer element and a second buffer flow resistance associated with said gaseous anesthetic line connection buffer element for limiting an influx of the gaseous components into a gaseous anesthetic volume of said gaseous anesthetic line connection buffer element wherein said fresh gas line connection buffer element and said gaseous anesthetic line connection buffer element have respective volumes dimensioned, in conjunction with said first buffer flow resistance and said second flow resistance to limit the influx of the gaseous components into said buffer volumes, such that a response behavior to pressure changes, of said first buffer flow resistance with said fresh gas line connection buffer element and said second buffer flow resistance with said gaseous anesthetic line connection buffer element, is characterized by time constants, that are higher than time constants that characterize a response behavior to pressure changes of said fresh gas line with said fixed resistance and said gaseous anesthetic line with said variable flow resistance.

12. An anesthetic dispensing device arrangement in accordance with claim 10, wherein characteristic response times to pressure changes in the interior of said buffer elements are longer than the characteristic response times to pressure changes in said lines for supplying the gaseous components, by at least one order of magnitude.

13. An anesthetic dispensing device arrangement in accordance with claim 10, wherein a flow path of said fresh gas line connection between said fresh gas line and said fresh gas line connection buffer element and a flow path of said gaseous anesthetic line connection between said gaseous anesthetic line and said gaseous anesthetic line connection buffer element each have a higher flow resistance than a flow resistance of said line for supplying the gaseous anesthetic.

14. An anesthetic dispensing device arrangement in accordance with claim 10, wherein said fresh gas line connection buffer element includes a flow resistance means that defines a flow resistance in a flow path between said fresh gas line and said fresh gas line connection buffer and said gaseous anesthetic line connection buffer element includes a flow resistance means that defines a flow resistance in a flow path between said gaseous anesthetic line and said gaseous anesthetic line connection buffer.

15. An anesthetic dispensing device arrangement in accordance with claim 14, wherein each of said flow resistance means comprise an aperture through which gaseous components can flow into said buffer elements.

16. An anesthetic dispensing device arrangement in accordance with claim 15, wherein said apertures have a diameter of at most 150 μm and said buffer elements have a volume of at least 0.2 mL.

17. An anesthetic dispensing device arrangement in accordance with claim 15, wherein said apertures have a diameter of 100 μm and said buffer elements have a volume of 1 mL.

18. A device for measuring a differential pressure in anesthetic dispensing devices, the device comprising:
a first gas supply line leading to a mixing site for supplying a gaseous component to said mixing site;
a second gas supply line leading to said mixing site for supplying another gaseous component to said mixing site;
a differential pressure sensor;
a first gas connection measuring line for connection of said differential pressure sensor with said first gas supply line;
a second gas connection measuring line for connection of said differential pressure sensor with said second gas supply line, said differential pressure sensor for measuring a differential pressure between said first gas connection measuring line and said second gas connection measuring line;
a first buffer element integrated in said first gas connection measuring line between said first gas supply line and said differential pressure sensor; and
a second buffer element integrated in said second gas connection measuring line between said second gas supply line and said differential pressure sensor.

19. An anesthetic dispensing device arrangement in accordance with claim 18, wherein said first gas supply line is a gaseous anesthetic line with a variable flow resistance and said second gas supply line is fresh gas line with a fixed resistance.

20. An anesthetic dispensing device arrangement in accordance with claim 19, further comprising a first buffer flow resistance associated with said first buffer element for limiting an influx of gas into a volume of said first buffer element and a second buffer flow resistance associated with said second buffer element for limiting an influx of gas into a volume of said second buffer element.

* * * * *